United States Patent
Zhu

(10) Patent No.: US 8,013,168 B2
(45) Date of Patent: Sep. 6, 2011

(54) 2-{(R)-2-METHYLPYRROLIDIN-2-YL)-1H-BENZIMIDAZOLE-4-CARBOXAMIDE CRYSTALLINE FORM 2

(75) Inventor: Gui-Dong Zhu, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 396 days.

(21) Appl. No.: 12/248,988

(22) Filed: Oct. 10, 2008

(65) Prior Publication Data

US 2009/0099246 A1 Apr. 16, 2009

Related U.S. Application Data

(60) Provisional application No. 60/979,654, filed on Oct. 12, 2007.

(51) Int. Cl.
*C07D 403/04* (2006.01)
(52) U.S. Cl. .................................. 548/304.7
(58) Field of Classification Search ............... 548/304.7
See application file for complete search history.

(56) References Cited

U.S. PATENT DOCUMENTS 7,550,603 B2 * 6/2009 Zhu et al. .................. 548/304.7
2006/0229289 A1 10/2006 Zhu et al.

FOREIGN PATENT DOCUMENTS

WO WO2009/049111 A1 4/2009

OTHER PUBLICATIONS

ISR for International application No. PCT/US2008/079439(9108WO01), 2008.
ISR for International application No. PCT/US2008/079441, 2008.
Co-pending Application U.S. Appl. No. 11/401,638, 2006.
Co-pending Application U.S. Appl. No. 12/248,972, 2008.
Alvarez R.M., Propiedad Intelectual e Innovacion Technologica en El Ecuador, Abya-Yala, ed., 2000, pp. 37-39.
Aulton M.E., ed., Pharmaceutics: The Science of Dosage Form Design, 2nd Edition, Churchill Livingstone, 2004, Table of Contents.
Correa., "Pautas para el examen de patentes farmaceuticas. Una perspective desde la Salud Publica", 2006.
Garrido J., "Influencia De Los Agentes Exteriores Sobre La Forma De Los Cristales" in: Forma y Estructura De Los Cristales, Chapter 5, Alhambra, 1973, pp. 204-225.
Hilfiker R., ed., Polymorphism in the Pharmaceutical Industry, Wiley-VCH Verlag GmbH & Co, 2006, Table of Contents.
Lien E.J., et al., "Atomic and Molecular Structure and the States of Matter" in: Pharmaceutical Sciences, Chapter 13, Remington J.P., ed., Mack Publishing Company, 1980, pp. 160-181.
Spanish Minerals: X-rays and the Diffraction by Crystals. [online], [retrieved on Nov. 5, 2010]. Retrievd from the Internet< URL:http://translate.googleusercontentcom/translate_c?hl=en&sl=es&u=http://www.spanishmi.

* cited by examiner

*Primary Examiner* — Rei-tsang Shiao
(74) *Attorney, Agent, or Firm* — Susan L. Steele; Rachel A. Polster

(57) ABSTRACT

2-((R)-2-Methylpyrrolidin-2-yl)-1H-benzimidazole-4-carboxamide Crystalline Form 2, ways to make it, compositions comprising it and made using it, and methods of treating patients having disease using it are disclosed.

6 Claims, 8 Drawing Sheets

2-{(R)-2-METHYLPYRROLIDIN-2-YL)-1H-BENZIMIDAZOLE-4-CARBOXAMIDE CRYSTALLINE FORM 2

This application claims priority from U.S. Provisional Patent Application Ser. No. 60/979,654, filed Oct. 12, 2007, incorporated herein by reference.

FIELD OF THE INVENTION

This invention pertains to 2-((R)-2-Methylpyrrolidin-2-yl)-1H-benzimidazole-4-carboxamide, also referred to herein as ABT-888, Crystalline Form 2, ways to make it, compositions comprising it and made using it, and methods of treating patients having disease using it.

BACKGROUND OF THE INVENTION

Poly(ADP-ribose)polymerase (PARP) has an essential role in facilitating DNA repair, controlling RNA transcription, mediating cell death and regulating immune response. PARP inhibitors have demonstrated efficacy in a number of disease models, such as, for example, 2-((R)-2-methylpyrrolidin-2-yl)-1H-benzimidazole-4-carboxamide (ABT-888) that has shown to limit tumor growth in tumor-bearing animals.

Crystallinity of ABT-888 may effect, among other physical and mechanical properties, its stability, solubility, dissolution rate, hardness, compressability and melting point. Because ease of manufacture and formulation of ABT-888 is dependent on some, if not all, of these properties, there is an existing need in the chemical and therapeutic arts for identification of crystalline forms of ABT-888 and ways to reproducibly make them.

SUMMARY OF THE INVENTION

Figure 1:
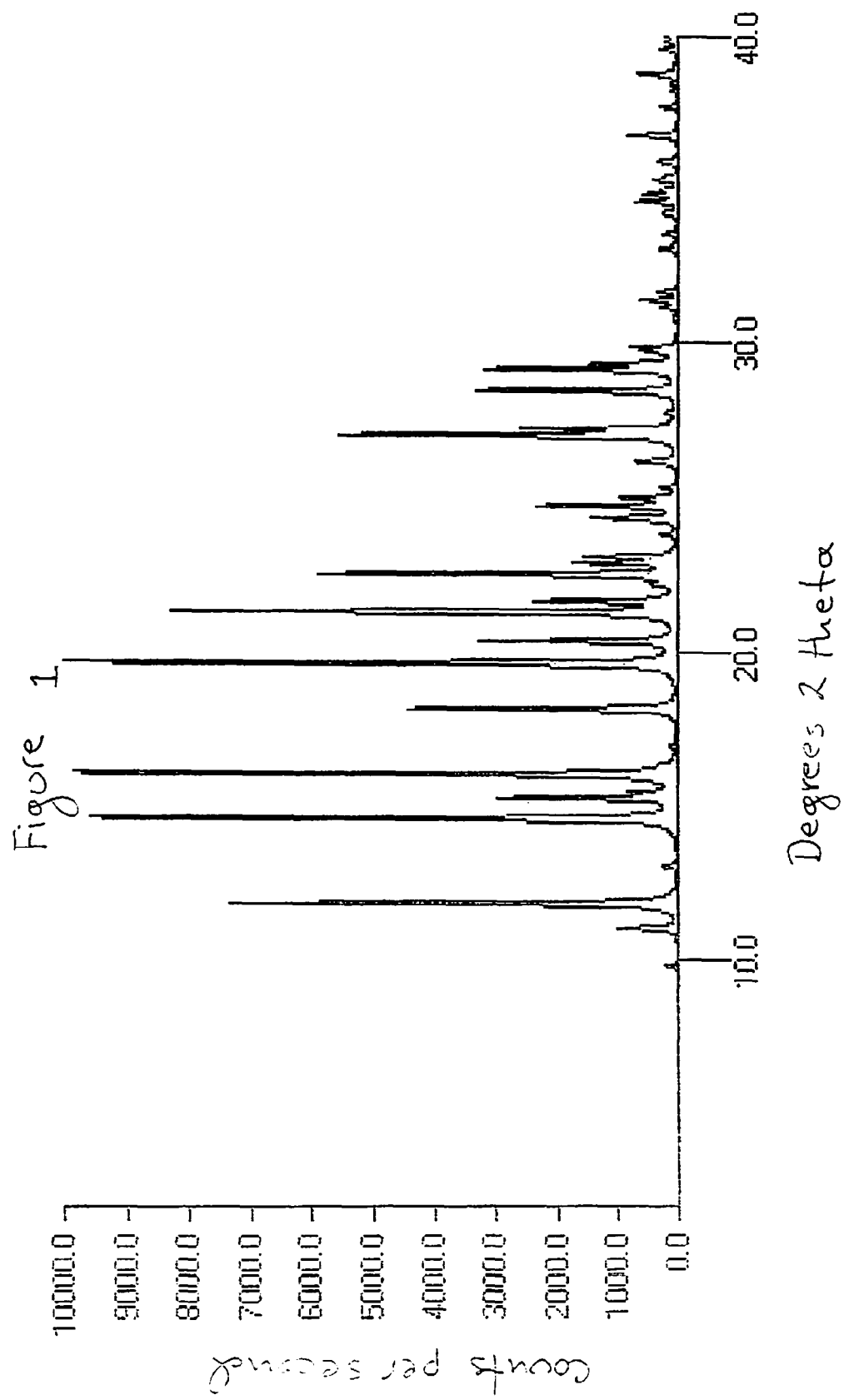
FIG. 1 shows a theoretical powder X-ray diffraction (PXRD) spectrum of ABT-888 Crystalline Form 1.
Figure 2:
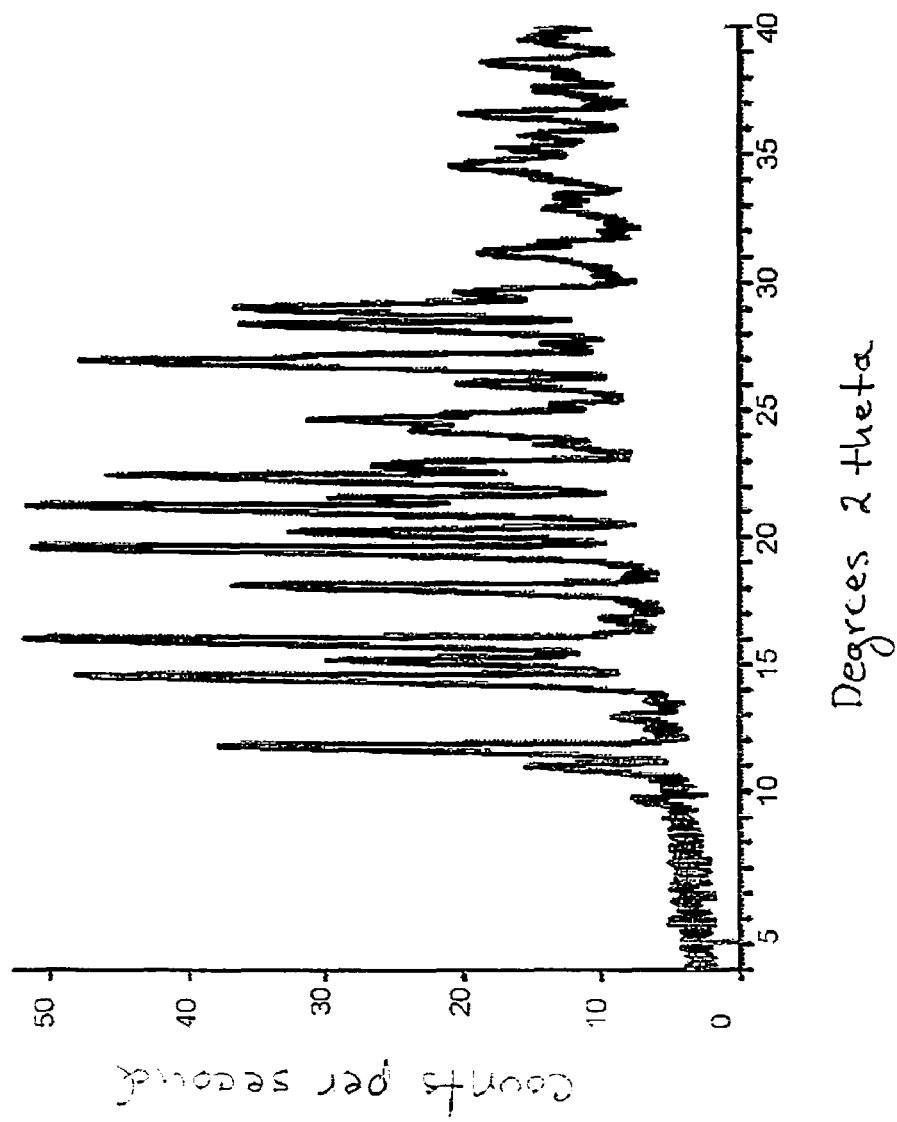
FIG. 2 shows an experimental PXRD spectrum of ABT-888 Crystalline Form 1.
Figure 3:
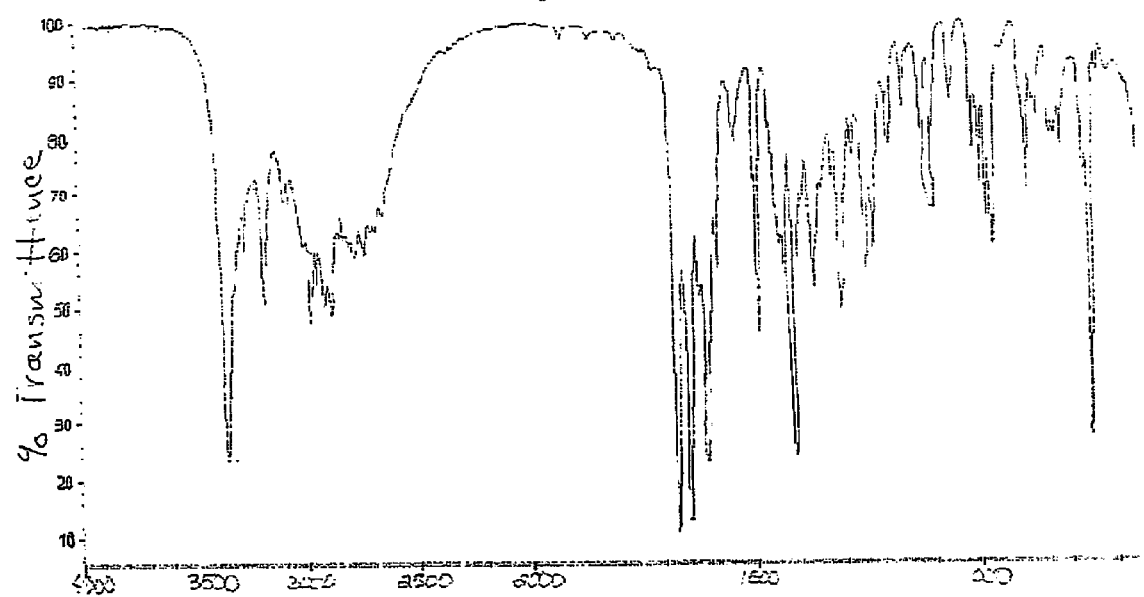
FIG. 3 shows the infra red (FT/IR) spectrum of ABT-888 Crystalline Form 1.
Figure 4:
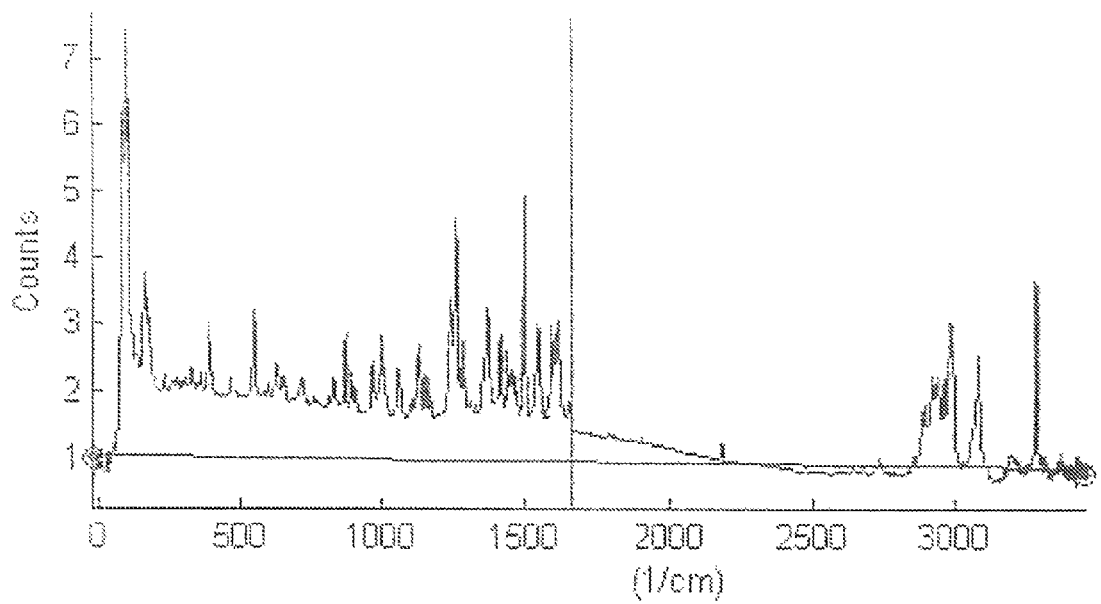
FIG. 4 shows the Raman spectrum of ABT-888 Crystalline Form 1.
Figure 5:
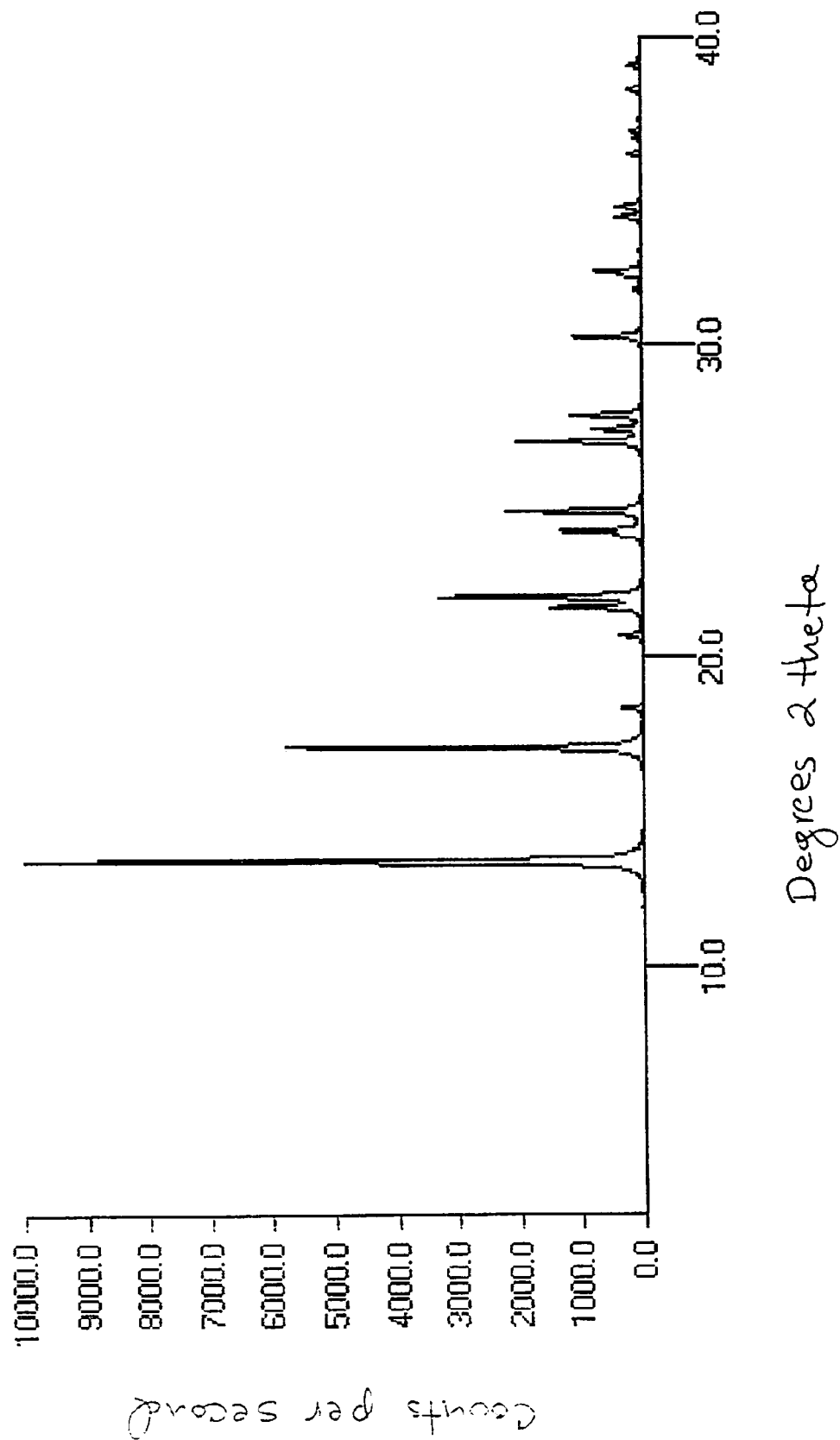
FIG. 5 shows a theoretical PXRD spectrum of ABT-888 Crystalline Form 2.
Figure 6:
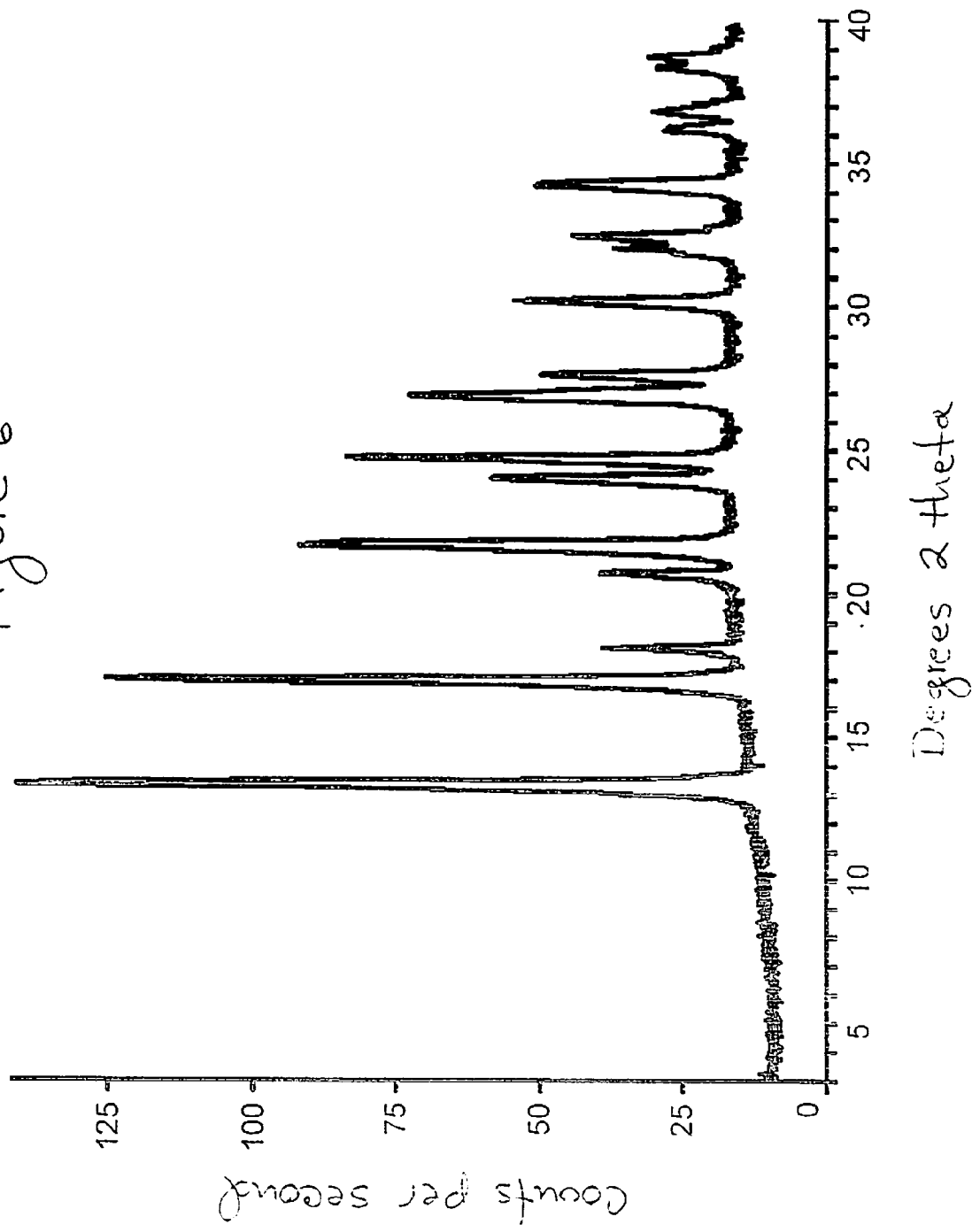
FIG. 6 shows an experimental PXRD spectrum of ABT-888 Crystalline Form 2.
Figure 7:
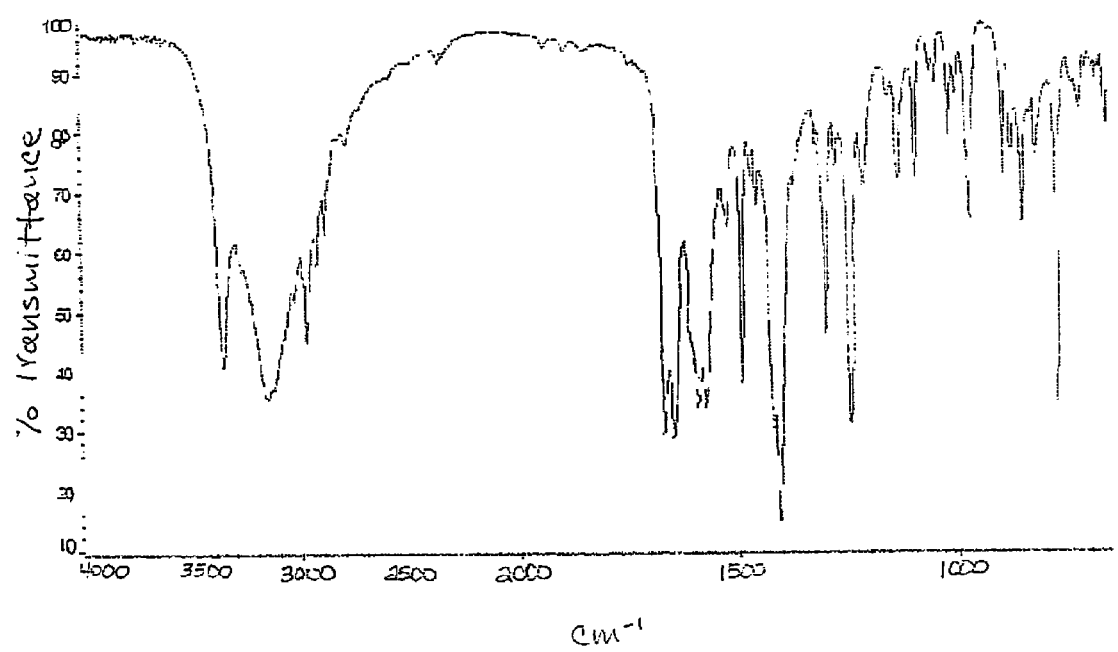
FIG. 7 shows the infra red (FT/IR) spectrum of ABT-888 Crystalline Form 2.
Figure 8:
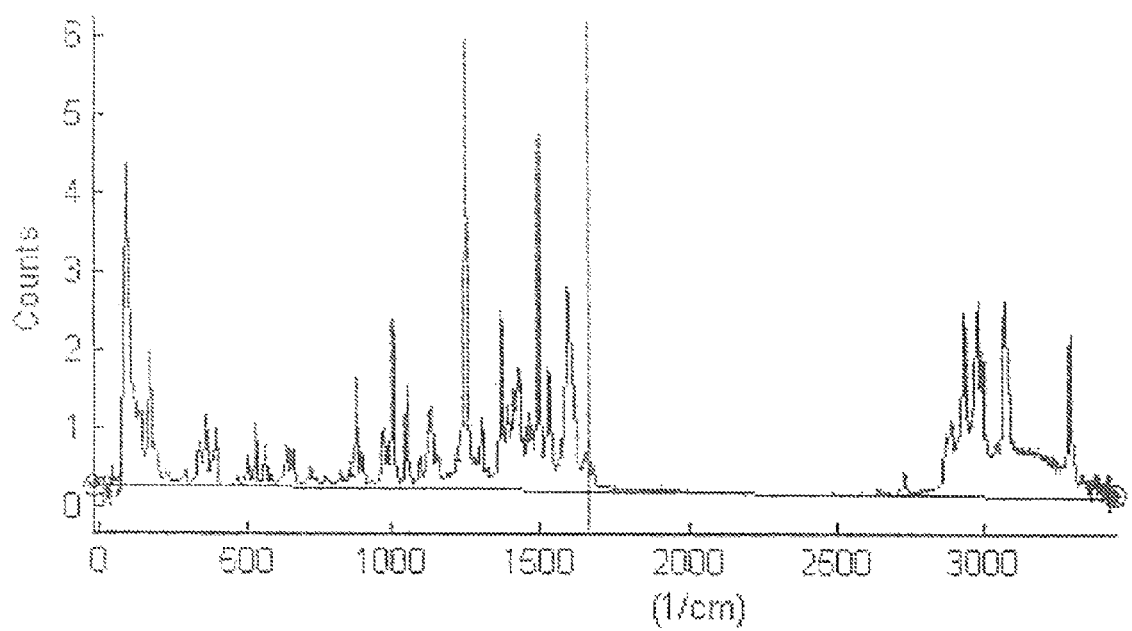
FIG. 8 shows the Raman spectrum of ABT-888 Crystalline Form 2.

One embodiment of this invention pertains to 2-((R)-2-Methylpyrrolidin-2-yl)-1H-benzimidazole-4-carboxamide Crystalline Form 2 which, when measured at about −100° C. in the trigonal crystal system and $P3_2$ space group with radiation at 0.7107 Å, is characterized by respective lattice parameter values a, b and c of 8.599 Å±0.002 Å, 8.599 Å±0.002 Å and 14.526 Å±0.006 Å and respective $\alpha$, $\beta$ and $\gamma$ values of 90°, 90° and 120°.

Another embodiment pertains to 2-((R)-2-Methylpyrrolidin-2-yl)-1H-benzimidazole-4-carboxamide Crystalline Form 2 which, when measured at about 25° C. with radiation at 1.54178 Å, is characterized by a powder diffraction pattern having at least three respective 2θ values of about 13.4°, 17.1°, 21.6°, 21.9°, 24.1°, 24.7°, 26.9°, 27.3°, 27.8°, 30.3°, 32.4° and 34.2° and essentially without peaks below about 11.5°.

Still another embodiment pertains to compositions comprising an excipient and 2-((R)-2-Methylpyrrolidin-2-yl)-1H-benzimidazole-4-carboxamide Crystalline Form 2 which, when measured at about −100° C. in the trigonal crystal system and $P3_2$ space group with radiation at 0.7107 Å, is characterized by respective lattice parameter values a, b and c of 8.599 Å±0.002 Å, 8.599 Å±0.002 Å and 14.526 Å±0.006 Å and respective $\alpha$, $\beta$ and $\gamma$ values of 90°, 90° and 120°.

Another embodiment pertains to compositions comprising an excipient and 2-((R)-2-Methylpyrrolidin-2-yl)-1H-benzimidazole-4-carboxamide Crystalline Form 2 which, when measured at about 25° C. with radiation at 1.54178 Å, is characterized by a powder diffraction pattern having respective 2θ values of about 9.9°, 11.0° and 11.8° and one or more than one additional peaks having respective 2θ values of about 13.4°, 17.1°, 21.6°, 21.9°, 24.1°, 24.7°, 26.9°, 27.3°, 27.8°, 30.3°, 32.4° and 34.2° and essentially without peaks below about 11.5°.

Still another embodiment pertains to methods of treating cancer in a mammal comprising administering thereto, with or without one or more than one additional anticancer drugs, a therapeutically effective amount of 2-((R)-2-Methylpyrrolidin-2-yl)-1H-benzimidazole-4-carboxamide Crystalline Form 2 which, when measured at about −100° C. in the trigonal crystal system and $P3_2$ space group with radiation at 0.7107 Å, is characterized by respective lattice parameter values a, b and c of 8.599 Å±0.002 Å, 8.599 Å±0.002 Å and 14.526 Å±0.006 Å and respective $\alpha$, $\beta$ and $\gamma$ values of 90°, 90° and 120°.

Still another embodiment pertains to methods of treating cancer in a mammal comprising administering thereto, with or without one or more than one additional anticancer drugs, a therapeutically effective amount of 2-((R)-2-Methylpyrrolidin-2-yl)-1H-benzimidazole-4-carboxamide Crystalline Form 2 which, when measured at about 25° C. with radiation at 1.54178 Å, is characterized by a powder diffraction pattern having respective 2θ values of about 13.4°, 17.1°, 21.6°, 21.9°, 24.1°, 24.7°, 26.9°, 27.3°, 27.8°, 30.3°, 32.4° and 34.2° and essentially without peaks below about 1.5°.

Still another embodiment pertains to a process for making 2-((R)-2-Methylpyrrolidin-2-yl)-1H-benzimidazole-4-carboxamide Crystalline Form 2, comprising:

making 2-((R)-2-methylpyrrolidin-2-yl)-1H-benzimidazole-4-carboxamide;

providing a mixture comprising 2-((R)-2-methylpyrrolidin-2-yl)-1H-benzimidazole-4-carboxamide and solvent, wherein the 2-((R)-2-methylpyrrolidin-2-yl)-1H-benzimidazole-4-carboxamide is completely dissolved in the solvent;

causing 2-((R)-2-Methylpyrrolidin-2-yl)-1H-benzimidazole-4-carboxamide Crystalline Form 2 to exist in the mixture, which 2-((R)-2-Methylpyrrolidin-2-yl)-1H-benzimidazole-4-carboxamide Crystalline Form 2, which, when isolated and measured at about −100° C. in the trigonal crystal system and $P3_2$ space group with radiation at 0.7107 Å, is characterized by respective lattice parameter values a, b and c of 8.599 Å±0.002 Å, 8.599 Å±0.002 Å and 14.526 Å±0.006 Å and respective $\alpha$, $\beta$ and $\gamma$ values of 90°, 90° and 120°; and isolating the 2-((R)-2-Methylpyrrolidin-2-yl)-1H-benzimidazole-4-carboxamide Crystalline Form 2.

Still another embodiment comprises 2-((R)-2-Methylpyrrolidin-2-yl)-1H-benzimidazole-4-carboxamide Crystalline Form 2 prepared by the process of the preceeding embodiment.

Still another embodiment comprises 2-((R)-2-Methylpyrrolidin-2-yl)-1H-benzimidazole-4-carboxamide Crystalline Form 2 prepared by the process of the preceeding embodiment.

Still another embodiment comprises a mono-acid or di-acid salt of 2-((R)-2-Methylpyrrolidin-2-yl)-1H-benzimidazole-4-carboxamide for use in preparing 2-((R)-2-Methylpyrrolidin-2-yl)-1H-benzimidazole-4-carboxamide Crystalline Form 2.

Still another embodiment comprises 2-((R)-2-Methylpyrrolidin-2-yl)-1H-benzimidazole-4-carboxamide dihydrochloride for use in preparing 2-((R)-2-Methylpyrrolidin-2-yl)-1H-benzimidazole-4-carboxamide Crystalline Form 2.

Still another embodiment comprises amorphous 2-((R)-2-Methylpyrrolidin-2-yl)-1H-benzimidazole-4-carboxamide for use in preparing 2-((R)-2-Methylpyrrolidin-2-yl)-1H-benzimidazole-4-carboxamide Crystalline Form 2.

Still another embodiment comprises 2-((R)-2-Methylpyrrolidin-2-yl)-1H-benzimidazole-4-carboxamide Crystalline Form 1 for use in preparing 2-((R)-2-Methylpyrrolidin-2-yl)-1H-benzimidazole-4-carboxamide Crystalline Form 2.

DETAILED DESCRIPTION OF THE INVENTION

This invention pertains to discovery of 2-((R)-2-methylpyrrolidin-2-yl)-1H-benzimidazole-4-carboxamide, also referred to herein as ABT-888, Crystalline Form 2, ways to make it, ways to characterize it, compositions containing it and made with it, and methods of treating cancer using it. The terms "2-((R)-2-Methylpyrrolidin-2-yl)-1H-benzimidazole-4-carboxamide" and "ABT-888" are meant to be used interchangeably.

The terms "ABT-888" and "an ABT-888" without any indicia of crystallinity or non-crystallinity associated with it, as used herein, mean amorphous ABT-888, a crystalline ABT-888 such as ABT-888 Crystalline Form 1 or ABT-888 Crystalline Form 2, microcrystalline ABT-888, ABT-888 in solution, a semisolid, wax or oil form of ABT-888, mixtures thereof and the like.

The terms "crystalline" and "microcrystalline," as used herein, mean having a regularly repeating arrangement of molecules which is maintained over a long range or external face planes.

The term "crystalline ABT-888," as used herein, means a particular crystalline ABT-888, including the crystalline ABT-888 of this invention, i.e. ABT-888 Crystalline Form 2.

The term "crystalline ABT-888 of this invention," as used herein, means a metastable crystalline form of ABT-888 at 25° C., i.e. ABT-888 Crystalline Form 2 which, when measured at about −100° C. in the trigonal crystal system and $P3_2$ space group with radiation at 0.7107 Å, is characterized by respective lattice parameter values a, b and c of 8.599 Å±0.002 Å, is 8.599 Å±0.002 Å and 14.526 Å±0.006 Å and respective α, β and γ values of 90°, 90° and 120° or which, when measured at about 25° C. with radiation at 1.54178 Å, is characterized by a powder diffraction pattern having respective 2θ values of about 13.4° (1,0,1), 17.1° (1,0,2), 21.6° (1,1,1), 21.9° (1,0,3), 24.1° (1,1,2), 24.7° (2,0,1), 26.9° (2,0,2), 27.3° (1,0,4), 27.8° (1,1,3), 30.3° (2,0,3), 32.4° (2,1,1), and 34.2° (2,1,2), and essentially without peaks below about 11.5° wherein the absorptions are shown with their corresponding Miler Index (h,k,l) values.

The term "amorphous," as used herein, means a supercooled liquid substance or a viscous liquid which appears as a solid but does not have a regularly repeating arrangement of molecules which is maintained over a long range. Amorphous substances do not have melting points but rather soften or flow above a certain temperature known as the glass transition temperature.

The term "semisolid ABT-888," as used herein, means a combination of ABT-888 and solvent in a gelatinous enough state to prevent passage through a semi-permeable membrane or filter.

It is meant to be understood that when peak positions are further used to identify a particular crystalline form of a compound when unit cell parameters of the compound are used in combination therewith, any one peak position or combination of peak positions may be used to further identify the particular crystalline form.

Unless stated otherwise, percentages herein are weight/weight (w/w) percentages.

The term "solvent," as used herein, means a liquid in which a compound is soluble or partially soluble enough at a given concentration to dissolve or partially dissolve the compound.

The term "anti-solvent," as used herein, means a liquid in which a compound is insoluble enough at a given concentration to be effective for precipitating that compound from a solution.

Solvents and anti-solvents may be mixed with or without separation of phases.

It is meant to be understood that, because many solvents and anti-solvents contain impurities, the level of impurities in solvents and anti-solvents for the practice of this invention, if present, are at a low enough concentration that they do not interfere with the intended use of the solvent in which they are present.

The term "acid," as used herein, means a compound having at least one acidic proton. Examples of acids for the practice of this invention include, but are not limited to, hydrochloric acid, hydrobromic acid, trifluoroacetic acid, trichloroacetic acid, sulfuric acid, phosphoric acid and the like.

The term "base," as used herein, means a compound capable of accepting a proton. Examples of bases for the practice of this invention include, but are not limited to, sodium carbonate, sodium bicarbonate, potassium carbonate, potassium bicarbonate triethylamine, diisopropylethylamine and the like.

Causing ABT-888 Crystalline Form 2 to exist in a mixture comprising ABT-888 and solvent, wherein the ABT-888 has completely dissolved, is known as nucleation.

For the practice of this invention, nucleation may be made to occur by means such as solvent removal, temperature change, solvent-miscible anti-solvent addition, solvent-immiscible anti-solvent addition, seed crystal addition of ABT-888 Crystalline Form 2, chafing or scratching the interior of the container, preferably a glass container, in which nucleation is meant to occur with an implement such as a glass rod or a glass bead or beads, or a combination of the foregoing.

For the practice of this invention, nucleation may be followed by crystal growth, accompanied by crystal growth, or followed and accompanied by crystal growth during which, and as a result of which, the percentage of ABT-888 Crystalline Form 2 increases.

It is meant to be understood that airborne seeds (seed crystals) of crystalline ABT-888 Crystalline Form 2 may also cause nucleation in a mixture of ABT-888 Crystalline Form 2 and solvent in which the ABT-888 his completely dissolved.

The term "seed crystal," as used herein, means a particular crystalline form of a substance having mass. It is meant to be understood that such a crystal may be small enough to be airborne or invisible to the eye without means of detection.

The term "isolating" as used herein, means separating ABT-888 Crystalline Form 2 and solvent, anti-solvent, or a mixture of solvent anti-solvent. This is typically accomplished by means such as centrifugation, filtration with or without vacuum, filtration with positive pressure, distillation, evaporation or a combination thereof.

Therapeutically acceptable amounts of ABT-888 Crystalline Form 2 depend on recipient of treatment, disorder being treated and severity thereof, composition containing it, time of administration, route of administration, duration of treatment, its potency, its rate of clearance and whether or not another drug is co-administered. The amount of ABT-888 Crystalline Form 2 used to make a composition to be administered daily to a patient in a single dose or in divided doses is from about 0.03 to about 200 mg/kg body weight. Single dose compositions contain these amounts or a combination of submultiples thereof.

ABT-888 Crystalline Form 2 may be administered with or without an excipient. Excipients include but are not limited to, for example, encapsulating materials and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising or made with ABT-888 Crystalline Form 2 to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like.

Excipients for preparation of compositions comprising or made with ABT-888 Crystalline Form 2 to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like.

Excipients for preparation of compositions comprising or made with ABT-888 Crystalline Form 2 to be administered osmotically include, for example, chlorofluorohydrocarbons, ethanol, water, mixtures thereof and the like.

Excipients for preparation of compositions comprising or made with ABT-888 Crystalline Form 2 to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like.

Excipients for preparation of compositions comprising or made with ABT-888 Crystalline Form 2 to be administered rectally or vaginally include, but are not limited to, cocoa butter, polyethylene glycol, wax, mixtures thereof and the like.

Preparation of ABT-888 and its utility as a PARP inhibitor is described in commonly-owned United States Patent Application Publication No. 2006/0229289.

The hydrochloride salt of ABT-888 is disclosed in commonly-owned United States Patent Application Publication No. 2006/0229289.

ABT-888 Crystalline Form 2 is useful when administered with anticancer drugs such as alkylating agents, angiogenesis inhibitors, antibodies, antimetabolites, antimitotics, antiproliferatives, aurora kinase inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, CloretazineTm (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1 152, MLN-8054, VX-680 and the like.

Bcr-Abl kinase inhibitors include DASATINIB (BMS-354825), GLEEVEC (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), Herceptin (trastuzumab), TYKERB® (lapatinib), OMNITARG® (2C4, petuzumab), TAK-165, GW-572016 (ionafamib), GW-282974, EKB-569, PI-166, dHER2 (HER2 vaccine), APC-8024 (HER-2 vaccine), anti- HER/2neu bispecific antibody, B7.her2TgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FCl, PU-3 , radicicol, SNX-2112, STA-9090 VER49009 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENEL® (piroxicam) ibuprofin cream, ALEVEL® and NAPROSYNR® (naproxen), VOLTAREN® (diclofenac), INDOCIN® (indomethacin), CLINORIL® (sulindac), TOLECTIN® (tolmetin), LODINEL® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATINR® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN (bevacizumab), ABT-869, AEE-788 , ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787 , ZK-222584), SUTENT® (sunitinib, SU-11248), VEGF trap, vatalanib, ZACTIMA™ (vandetanib, ZD-6474) and the like.

Antimetabolites include ALIMTA® (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZARR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38 , tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Deltoids and retinoids include seocalcitol (EB 1089, CB 1093), lexacalcitrol (KH 1060), fenretinide, PANRETIN® (aliretinoin), ATRAGEN® (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1 , combinations thereof and the like. Other agents include ALFAFERONEL®, BAM-002 , BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, ABT-888 Crystalline Form 2 may be combined with other chemptherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane (1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906, GARDASIL® (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSI-DEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), Taxoprexin® (DHA-paclitaxel), TELCYTA™ (TLK286), temilifene, TEMODAR® (temozolomide), tesmilifene, thalidomide, THERATOPEL (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

It is also expected that ABT-888 Crystalline Form 2 would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

The following examples are presented to provide what is believed to be the most useful and readily understood description of procedures and conceptual aspects of this invention.

EXAMPLE 1

Preparation of ABT-888 Crystalline Form 1

A mixture of ABT-888 dihydrochloride (10 g) was stirred in saturated potassium bicarbonate (50 mL) and n-butanol (50 mL) until the ABT-888 dihydrochloride completely dissolved. The aqueous layer was extracted with a second portion of n-butanol then discarded. The extracts were combined, washed with 15% sodium chloride solution (50 mL) and concentrated. The concentrate was chase distilled three times with heptane (50 mL),dissolved in refluxing 2-propanol (45 mL) and filtered hot. The filtrate was cooled to ambient temperature with stirring over 18 hours, cooled to 0-5° C., stirred for 1 hour, and filtered. The filtrant was washed with 2-propanol and dried in a vacuum oven at 45-50° C. with a slight nitrogen purge.

EXAMPLE 2

Preparation of ABT-888 Crystalline Form 2

A mixture of ABT-888 in methanol, in which the ABT-888 was completely dissolved, was concentrated at about 35° C., and the concentrate was dried to a constant weight.

Powder X-ray diffraction was performed using an XDS-2000/X-ray diffractometer equipped with a 2 kW normal focus X-ray tube and a Peltier cooled germanium solid-state detector (Scintag Inc., Sunnyvale, Calif.). The data were processed using DMSNT software (version 1.37). The X-ray source was a copper filament (Cu-Kα at 1.54178 Å) operated at 45 kV and 40 mA. The alignment of the goniometer was checked daily using a Corundum standard. The sample was placed in a thin layer (with no prior grinding) onto a zero background plate and continuously scanned at a rate of 2°2θ per minute over a range of 2°-40° 2θ.

It is meant to be understood that relative intensities of peak heights in a PXRD pattern may vary and will be dependent on variables such as the temperature, size of crystal size or morphology, sample preparation, or sample height in the analysis well of the X-ray diffractometer.

It is also meant to be understood that peak positions may vary when measured with different radiation sources. For example, Cu-Kα$_1$, Mo-Kα, Co-Kα and Fe-Kα radiation, having wavelengths of 1.54060 Å, 0.7107 Å, 1.7902 Å and 1.9373 Å, respectively, may provide peak positions which differ from those measured with Cu-Kα radiation, which has a wavelength of 1.5478 Å.

The term "about" preceding a series of peak positions means that all of the peaks of the group which it precedes are reported in terms of angular positions (two theta) with an allowable variability of ±0.1° as specified by the U.S. Pharmacopeia, pages 1843-1884 (1995). The variability of ±0.1° is intended to be used when comparing two powder X-ray diffraction patterns. In practice, if a diffraction pattern peak from one pattern is assigned a range of angular positions (two theta) which is the measured peak position ±0.1° and if those ranges of peak positions overlap, then the two peaks are considered to have the same angular position. For example, if a peak from one pattern is determined to have a position of 11.0°, for comparison purposes the allowable variability allows the peak to be assigned a position in the range of 10.90°-111°.

Accordingly, for example, the phrase "about 13.4°, 17.1°, 21.6°, 21.9°, 24.1°, 24.7°, 26.9°, 27.3°, 27.8°, 30.3°, 32.4° and 34.2° and essentially without peaks below about 11.5°" means about 13.4°, about 17.1°, about 21.6°, about 21.9°, about 24.1°, about 24.7°, about 26.9°, about 27.3°, about 27.8°, about 30.3°, about 32.4° and about 34.2° and essentially without peaks below about 11.5° and also means 13.4°±0.1°, 17.1°±0.1°, 21.6°±0.1°, 21.9°±0.1°, 24.1°±0.1°, 24.7°±0.1°, 26.9°±0.1°, 27.3°±0.1°, 27.8°±0.1°, 30.3°±0.1°, 32.4°±0.1° and 34.2°±0.1° and essentially without peaks below about 11.5°±0.1°.

The term "about" preceding a temperature means the given temperature ±2° C. For example, about 25° C. means 25° C.±2° C. or 23° C.-27° C.

Raman spectra were measured using a laser Raman spectrometer (RamanRxn1 HTS-785 785 nm NIR laser and model HLS-L microprobe, with Holograms™ version 4.004.0.0230 and Holomap™ version 2.3.4 software, Kaiser Optical Systems, Inc., Ann Arbor, Mich.).

Transmission infrared spectra of the solids were obtained using a Fourier-transform infrared spectrometer (Nicolet Magna 750 FT-IR Spectrometer, Nicolet Instrument Corporation, Madison, Wis.) equipped with a Nicolet NIC-PLAN Microscope and MCT-A liquid nitrogen cooled detector. The sample was placed on a 13 mm×1 mm $BaF_2$ disc sample holder and 64 scans were collected at 4 $cm^{-1}$ resolution.

The foregoing is meant to be illustrative of the invention and not intended to limit it to the disclosed embodiments. Variations and changes obvious to one skilled in the art are intended to be within the scope and nature of the invention as defined in the claims.

I claim:

1. 2-((R)-2-Methylpyrrolidin-2-yl)-1H-benzimidazole-4-carboxamide Crystalline Form 2 which, when measured at about −100° C. in the trigonal crystal system and $P3_2$ space group with radiation at 0.7107 Å, is characterized by respective lattice parameter values a, b and c of 8.599 Å±0.002 Å, 8.599 Å±0.002 Å and 14.526 Å±0.006 Å and respective α, β and γ values of 90°, 90° and 120°.

2. 2-((R)-2-Methylpyrrolidin-2-yl)-1H-benzimidazole-4-carboxamide Crystalline Form 2 which, when measured at about 25° C. with radiation at 1.54178 Å, is characterized by a powder diffraction pattern having at least three respective 2θ values of about 13.4°, 17.1°, 21.6°, 21.9°, 24.1°, 24.7°, 26.9°, 27.3°, 27.8°, 30.3°, 32.4° and 34.2° and essentially without peaks below about 11.5°.

3. A composition comprising an excipient and 2-((R)-2-Methylpyrrolidin-2-yl)-1H-benzimidazole-4-carboxamide Crystalline Form 2 which, when measured at about 25° C. with radiation at 1.54178 Å, is characterized by a powder diffraction pattern having respective 2θ values of about 9.9°, 11.0° and 11.8° and one or more than one additional peaks having respective 2θ values of about 13.4°, 17.1°, 21.6°, 21.9°, 24.1°, 24.7°, 26.9°, 27.3°, 27.8°, 30.3°, 32.4° and 34.2° and essentially without peaks below about 11.5°.

4. A method of treating cancer in a mammal comprising administering thereto, with or without one or more than one additional anticancer drugs, a therapeutically effective amount of 2-((R)-2-Methylpyrrolidin-2-yl)-1H-benzimidazole-4-carboxamide Crystalline Form 2 which, when measured at about −100° C. in the trigonal crystal system and $P3_2$ space group with radiation at 0.7107 Å, is characterized by respective lattice parameter values a, b and c of 8.599 Å±0.002 Å, 8.599 Å±0.002 Å and 14.526 Å±0.006 Å and respective α, β and γ values of 90°, 90° and 120°.

5. A process for making 2-((R)-2-Methylpyrrolidin-2-yl)-1H-benzimidazole-4-carboxamide Crystalline Form 2, comprising:
   providing a mixture comprising 2-((R)-2-methylpyrrolidin-2-yl)-1H-benzimidazole-4-carboxamide and solvent, wherein the 2-((R)-2-methylpyrrolidin-2-yl)-1H-benzimidazole-4-carboxamide is completely dissolved in the solvent;
   causing 2-((R)-2-Methylpyrrolidin-2-yl)-1H-benzimidazole-4-carboxamide Crystalline Form 2 to exist in the mixture, which 2-((R)-2-Methylpyrrolidin-2-yl)-1H-benzimidazole-4-carboxamide Crystalline Form 2, which, when isolated and measured at about −100° C. in the trigonal crystal system and $P3_2$ space group with radiation at 0.7107 Å, is characterized by respective lattice parameter values a, b and c of 8.599 Å±0.002 Å, 8.599 Å±0.002 Å and 14.526 Å±0.006 Å and respective α, β and γ values of 90°, 90° and 120°.

6. The process of claim 5 further comprising isolating the 2-((R)-2-Methylpyrrolidin-2-yl)-1H-benzimidazole-4-carboxamide Crystalline Form 2.

* * * * *

UNITED STATES PATENT AND TRADEMARK OFFICE
CERTIFICATE OF CORRECTION

| | | |
|---|---|---|
| PATENT NO. | : 8,013,168 B2 | Page 1 of 1 |
| APPLICATION NO. | : 12/248988 | |
| DATED | : September 6, 2011 | |
| INVENTOR(S) | : Zhu | |

It is certified that error appears in the above-identified patent and that said Letters Patent is hereby corrected as shown below:

Title Page, Item (54) and at column 1, line 1, title: "2-{(R)-2-methylpyrrolidin-2-yl)" to read as --2-((R)-2-methylpyrrolidin-2-yl)--

Column 11, line 50, claim 1: "-100°C." to read as -- -100°C--

Column 12, line 06, claim 2: "25°C." to read as --25°C--

Column 12, line 13, claim 3: "25°C." to read as --25°C--

Column 12, line 16, claim 3: "one additional peaks" to read as --one additional peak--

Column 12, line 22, claim 4: "one additional anticancer drugs," to read as
--one additional anticancer drug,--

Column 12, line 25, claim 4: "-100°C." to read as -- -100°C--

Column 12, line 40, claim 5: "which 2-((R)-2-Methylpyrrolidin-2-yl)-1H-benzimidazole-4-carboxamide Crystalline Form 2," to read as --            -- (leave blank due to repeat)

Column 12, line 42, claim 5: "-100°C." to read as -- -100°C--

<div style="text-align: right;">

Signed and Sealed this
Fourth Day of September, 2012

David J. Kappos
*Director of the United States Patent and Trademark Office*

</div>